United States Patent [19]

Lifton

[11] Patent Number: 4,651,753
[45] Date of Patent: Mar. 24, 1987

[54] ENDOSCOPIC MULTIPLE BIOPSY INSTRUMENT
[75] Inventor: Lester J. Lifton, Mechanicsburg, Pa.
[73] Assignee: Jayco Pharmaceuticals, Camp Hill, Pa.
[21] Appl. No.: 659,998
[22] Filed: Oct. 12, 1984
[51] Int. Cl.⁴ .......................................... A61B 17/32
[52] U.S. Cl. ................................... 128/751; 128/753
[58] Field of Search .............. 128/749, 751, 752, 753, 128/754, 755

[56] References Cited
U.S. PATENT DOCUMENTS

| | | | |
|---|---|---|---|
| 3,416,531 | 12/1968 | Edwards | 128/656 |
| 3,844,272 | 10/1974 | Banko | 128/753 |
| 4,176,662 | 12/1979 | Frazer | 128/657 |
| 4,220,155 | 9/1980 | Kimberling et al. | 128/306 |
| 4,340,066 | 7/1982 | Shah | 128/749 |
| 4,461,305 | 7/1984 | Cibley | 128/751 |

FOREIGN PATENT DOCUMENTS
2453058 5/1976 Fed. Rep. of Germany ...... 128/751

Primary Examiner—Edward M. Coven
Attorney, Agent, or Firm—Millen & White

[57] ABSTRACT

A biopsy instrument for use with an endoscope includes a rigid cylindrical end attached to the distal end of a flexible arrangement of tubes. The rigid end comprises a cylindrical body having a cavity therein and said cavity extending towards the distal end of the body and being of a size sufficient to hold plural samples therein. Inside the body is a knife and suction generating device for drawing a biopsy sample into the cylindrical body and cutting it with the knife. Furthermore, a plunger is arranged coaxially with the knife for then pushing individual biopsy samples of a plurality into the distal end cavity of the cylindrical body.

9 Claims, 10 Drawing Figures

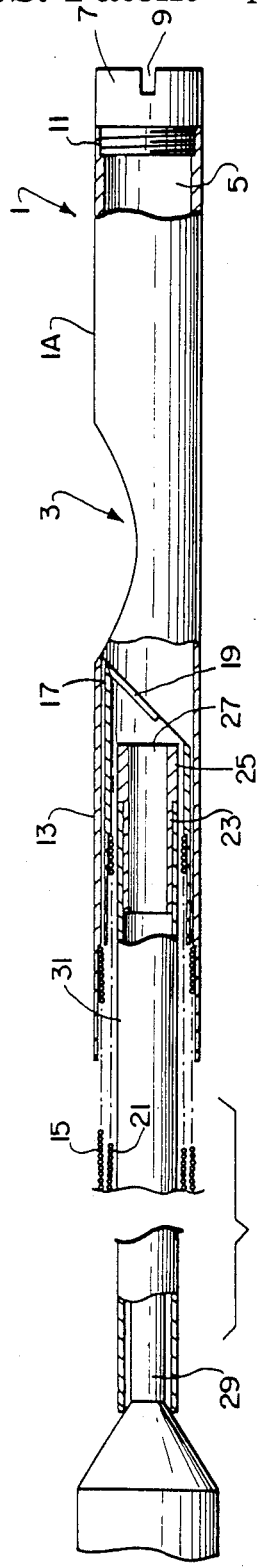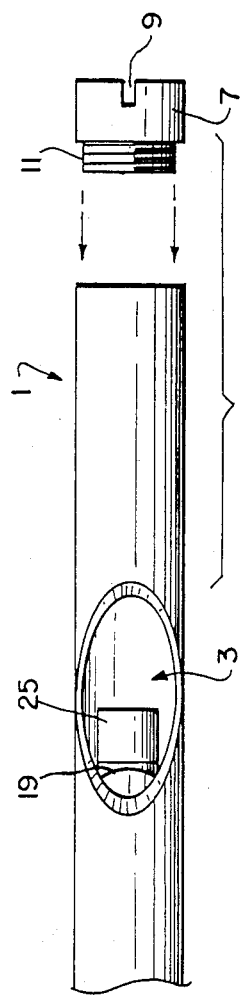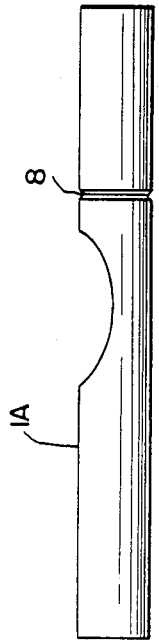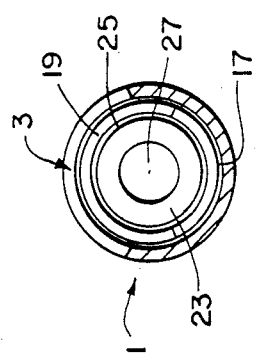

ENDOSCOPIC MULTIPLE BIOPSY INSTRUMENT

BACKGROUND OF THE INVENTION

This invention relates to a biopsy tool for use in conjunction with an endoscope, and more particularly to fit through a fiber-optic instrument into portions of a patient's body cavity for taking biopsy samples therefrom.

In the science of endoscopy, the technique of obtaining biopsies is performed by various methods. One standard technique includes the use of forceps consisting of two spheres which are attached by a pivot at one side. The spheres are closed by a scissor-like structure connected to a lone wire, which is pulled to close the biopsy spheres. In a recent development, a needle is inserted between the spheres to position the site to be biopsied for accurate removal. In order to conduct this method of obtaining biopsies samples, it is required that typically a 3 foot long biopsy forceps be inserted and removed for each biopsy, a very long, tedious and uncomfortable procedure.

A second method of obtaining biopsies, for example, in the small intestine, is the use of a non-endoscopic small bowel biopsy capsule. This device typically consists of a small capsule having an oval opening. Inside the capsule is a movable knife blade which can be triggered closed either by spring actuation or by hydraulic actuation. The biopsy is obtained by placing suction through a plastic tubing connected to the capsule and "sucking" the biopsy sample into the capsule. Thereafter, the knife is closed, cutting the biopsy. Such a device is disclosed, for example, in U.S. Pat. No. 3,590,808. In all but one of these types of constructions, the capsule is then removed from the body to obtain the biopsy. In the one exception, the biopsy is removed hydraulically from the capsule and multiple biopsies can thereby be obtained without removing the capsule. These types of devices are generally known as Carey and/or Crosby capsules.

All of the above-discussed devices suffer from the disadvantage that only single biopsies can be obtained after which the instrument must be withdrawn. Alternatively, the biopsies obtained are not sufficiently large to be adequately interpreted, and problems are encountered in maintaining the integrity of the specimen taken.

For discussions of other biopsy type or related devices, see U.S. Pat. No. 3,606,878; No. 3,902,498; No. 4,220,155; No. 3,033,194; No. 3,805,793; and No. 3,033,194.

SUMMARY OF THE INVENTION

It is thus an object of the present invention to provide a biopsy instrument capable of taking multiple biopsy samples without removal from site.

It is another object of the present invention to provide such an instrument constructed for use with an endoscopic instrument of the fiber-optic type whereby the biopsy instrument can be passed through the fiber-optic instrument and operated over a large distance.

Upon further study of the specification and appended claims, further objects and advantages of this invention will become apparent to those skilled in the art.

In accordance with the invention, the device is an improvement in endoscopic biopsy instruments capable of being passed through an endoscopic fiber-optic instrument. Such endoscopic biopsy instruments generally comprise a biopsy capsule with an oval opening, a movable knife blade in the capsule for cutting biopsy samples drawn into the capsule through said opening, and suction means for drawing the biopsy sample into the capsule prior to cutting.

The improvement in accordance with the invention provides that the capsule generally comprises a cylindrical body having a removable plug means at a distal end. The capsule also includes a proximal end and has a longitudinal axis. A curved surface extends proximately from the distal end of the body and has an opening therein into a sample receiving cavity extending into the body from the surface and toward the distal end thereof. As to the cavity itself, it is of a size sufficient to hold a plurality of biopsy samples therein, typically six, and a knife is reciprocable across the opening by means of knife actuating means operatively associated therewith for causing the knife to cut across the opening. In addition, sample pushing means is provided for pushing individual biopsy samples into the cavity toward the distal end of the body. In accordance with this construction, a plurality of individual biopsy samples can be taken and then removed from the biopsy instrument by removal of the plug means when the device is removed from a patient's body.

In a more specific aspect, the cylinder can be made of metal with the plug means being a screw plug. The cylinder will be attached by screw attachment or permanently soldered to a flexible, braided metallic tubing with the knife, which is also inside the cylinder and is constructed as a cylinder itself, being freely movable inside the outer casing of the cylinder and also respectively attached by screw attachment or permanently soldered to a flexible braided metallic tubing fitting inside the metallic tubing holding the outside casing tubing. Inside the knife cylinder is a third cylinder, i.e., the sample pushing means, which is preferably a plug pusher cylinder attached to plastic tubing which is either ultrasonically attached or glued to the plug, and which cylinder has a small opening at a flare at the distal end thereof sufficient to obtain adequate suction to pull the biopsy site into the capsule.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein:

FIG. 1 is a side view, in partial cross-section, of the biopsy instrument connected to its flexible metal tubing and actuating mechanisms for use obtaining biopsies;

FIG. 2 is a partial view from the top of the biopsy instrument with the plug means, i.e., a screw threaded plug, disassembled therefrom;

FIG. 4 is a cross-sectional view from the distal end of the instrument in accordance with the invention; and FIG. 5 is a side view of an additional embodiment of the biopsy storage chamber.

DETAILED DISCUSSION OF THE INVENTION

Figure 3A:
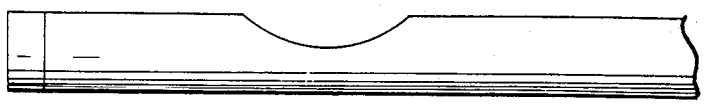
FIGS. 3A-3F shows the instrument in schematic diagram in accordance with the invention, in its sequence of operation, in taking and storing a biopsy sample.

In the Figures, like elements are numbered identically throughout the various Figures. As shown in FIG. 1, the instrument 1 in accordance with the invention consists of a metallic cylinder or cylindrical body 1A which is approximately 10-20 mm long, preferably about 15 mm long. For use with fiber-optic endoscopic instruments, the outside diameter must typically be 1.9-3.9 mm, with the metallic cylinder 1A being connected to a flexible tubing, for example braided metallic tubing capable of operation over a distance of 200 cm, and which has an outside diameter which is typically no greater than about 1.9 mm.

At the distal end of the cylinder 1A, is a removable plug 7. This plug 7, is preferably a screw threaded plug 7 having threads 11 for engaging a threaded interior wall portion at the distal end of the tubing 1A. In addition, the plug 7 includes cutout 9 to permit unscrewing from the metallic cylinder 1A and opening the distal end thereof by means of a tool, e.g., a screwdriver.

The cylinder 1A itself is generally hollow with a cylindrical wall defining cavity therein; and includes an oval, lateral opening 3 approximately one-half the circumference in width of its length extending longitudinally and circumferentially and communicating with the cavity. Typically the length will be 3-8 mm, and preferably about 5 mm. At the end of the cavity adjacent the plug 7, which is fixed to and closes the cavity is a storage chamber 5 wherein multiple biopsy samples, for example, six biopsies can be stored after taking of the biopsy samples without removing the instrument 1. In this regard, the device can be constructed to store up to 6 samples.

At the end opposite the plug 7, the cylinder 1A is attached also by screw attachment or permanently soldered to a, e.g., first flexible braided metallic tubing 15 as previously discussed for positioning the cylinder which will be capable of extending into the body a distance of up to about 200 cm as noted, and whose outside diameter will not exceed typically about 1.9 mm. Immediately inside the outside casing of the cylinder 1A is a knife blade 17, typically 5-9 cm long, and preferably about 6 cm long, which is also constructed in cylindrical configuration. The knife blade 17 is freely movable inside the outside casing and is also attached by screw attachment or permanently soldered typically to a second flexible braided metallic tubing 21 for reciprocating the knife which fits inside the tubing holding the outside casing tubing. The knife blade itself includes a cutting edge 19 as shown in FIGS. 1 and 2, which when the knife is reciprocated passes to close off the opening 3 into the cylinder. This is shown clearly in FIG. 2 from the top showing the sharp edge 19 of the knife 17. The opening 3 has a bevelled surface converging inwardly toward the cavity within the cylindrical body.

Inside an axial opening in the knife cylinder 17 is a third cylinder 23 having a flared end or rather relatively wide end 25 and a small opening or bore 27 of a size sufficient to generate suction therethrough for pulling a biopsy site into the cylinder 1A through the opening 3. The plug pusher cylinder 23 is attached to plastic tubing or other flexible tubing 31 to enable suction to be applied therethrough. Typically, as shown in FIG. 1 this will be done by means of a syringe, the tip 29 of which is attached to the plastic tubing 31 typically by a luer-lock tip inserted into the tubing. Thus, suction can be generated through the opening 27, which is more clearly shown in FIG. 4, and which also shows the general cylindrical configuration of the knife 17. The plug pusher cylinder 23 will generally be attached to the plastic tubing by either ultrasonic welding or glueing, and other than for the end openings thereof, will be sealed to the exterior.

Figure 3B:
Figure 3C:
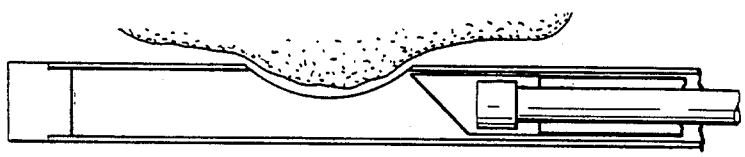
Figure 3D:
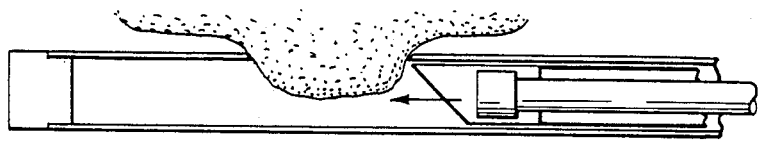
Figure 3E:
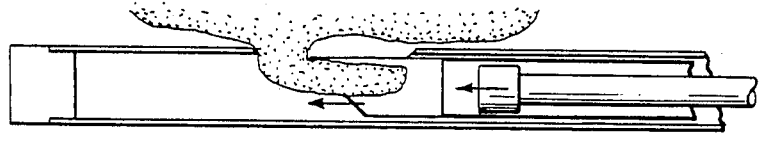
Figure 3F:
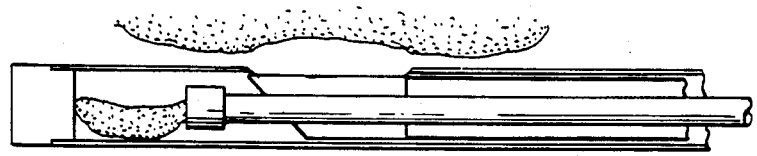

In operation, the sequence of obtaining a biopsy sample is generally shown in FIGS. 3A-3F. As shown in FIG. 3A the instrument tip is generally arranged within the region from which a biopsy sample is to be taken. FIG. 3B shows that the tip of the instrument will then be placed adjacent to the biopsy site, and in accordance with FIG. 3C, suction is applied to draw the biopsy site into the opening. Once the biopsy site is drawn into the opening, the cutting edge of the knife is advanced by being pushed with the broded cable 21 across the opening and as shown in FIG. 3E, tissue is cut by advancing the cutting edge. Finally, as shown in FIG. 3A, the biopsy is then pushed into the tip and stored, and this operation, in accordance with the preferred construction of the device can be repeated, typically about six times.

After the instrument is then removed from the body, the screw plug, or other type of construction plug can be removed, the metallic plug pusher pushed in again and the biopsies then extruded from the outside casing.

Although described above as a preferred embodiment, various alternative constructions for the invention can be employed. For instance, although screw type attachments are envisioned for the various flexible metallic tubings as well as for the outside plug, which in fact make the entire unit disassemblable and easily cleanable, permanent attachment can be provided to increase durability. The flexible tubing can be metallic braided tubing but flexible plastic tubing or other materials of sufficient strength can also be employed as will be evident to those of ordinary skill in this art.

As to the cylinder itself, although used as made of metal with a screw plug, the outside casing and plug thereof can also be constructed of plastic material with a snap-off end to permit easy disposing. Thus, a device is provided that can not only be used for both gastrointestinal and colonoscopic biopsies, but also to obtain samples, e.g., in a bronchoscopy, examination of the lungs utilizing a fiber-optic flexible bronchoscope.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. An endoscopic biopsy instrument for collecting tissue samples, the biopsy instrument having a diameter sufficiently small to be used with an endoscopic fiber-optic device, the instrument comprising:

a tubular body having a distal end and a proximal end, a lateral opening in the body positioned a selected distance from the distal end, the selected distance being sufficient to create a storage chamber within the tubular body to accommodate a plurality of tissue samples proximate the distal end of the tubular body;

an elongated flexible tube attached to the proximal end of the tubular body;

a removeable cap detachably secured to the distal end of the tubular body for allowing removal of tissue samples stored in the storage chamber of the tubular body through the distal end thereof upon detaching the cap from the distal end of the tubular body;

means for applying a vacuum within the tubular body to draw selected tissue samples through the lateral opening into the tubular body;

severing means having an axial opening therein, the severing means being longitudinally slidable within the tubular body past the lateral opening for severing a tissue sample from adjacent tissue; the severing means being separate from the storage chamber;

plunger means longitudinally slidable within the tubular body and within the axial opening in the severing means for pushing an individual severed tissue sample toward the cap and into the storage chamber and for pushing subsequently severed tissue samples toward the cap and into the storage chamber, and separate, flexible elongated means for separately reciprocating the severing means and the plunger means.

2. The endoscopic biopsy instrument of claim 1 wherein the means for applying the vacuum is coaxial with the plunger means.

3. An endoscopic biopsy instrument as in claim 1 wherein said tubular body is made of metal.

4. An endoscopic biopsy instrument as in claim 1 wherein the distal end of said tubular body has an interior wall which is threaded, and said removal cap includes a screw threaded portion for engagement with said threaded interior wall for closing said distal end.

5. An endoscopic biopsy instrument as in claim 1 wherein the flexible elongated means for reciprocating the plunger means is a hollow tube sealed with respect to the exterior, the plunger means having a bore communicating with its tube for allowing suction to occur in the tubular body through the hollow tube.

6. An endoscopic biopsy as in claim 1 wherein said cylindrical body is made of plastic.

7. An endoscopic biopsy instrument as in claim 6 wherein the cap is made of plastic, and is constructed integral with said tubular body in a snap-off structure.

8. An endoscopic biopsy instrument as in claim 1 wherein the severing means is generally cylindrically shaped with a sharp edge at the side adjacent the lateral opening into the cavity of the tubular body.

9. The instrument of claim 1 wherein the lateral opening has bevelled surface converging inwardly toward the cavity.

* * * * *